(12) United States Patent
Hidai et al.

(10) Patent No.: US 9,095,311 B2
(45) Date of Patent: Aug. 4, 2015

(54) BAND AND ELECTRONIC INSTRUMENT

(75) Inventors: Yoshihiro Hidai, Nagano (JP);
Shigemitsu Tanaka, Nagano (JP);
Mihoe Muramatsu, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 272 days.

(21) Appl. No.: 13/248,611

(22) Filed: Sep. 29, 2011

(65) Prior Publication Data

US 2012/0083674 A1 Apr. 5, 2012

(30) Foreign Application Priority Data

Sep. 30, 2010 (JP) ................................ 2010-221340

(51) Int. Cl.
*A61B 5/024* (2006.01)
*A61B 5/00* (2006.01)
*A44C 5/00* (2006.01)

(52) U.S. Cl.
CPC .............. *A61B 5/681* (2013.01); *A44C 5/0069* (2013.01); *A61B 5/6843* (2013.01); *A61B 5/02416* (2013.01); *A61B 5/02438* (2013.01)
USPC ........................................... 224/175; 24/164

(58) Field of Classification Search
USPC ......... 224/175, 164, 167, 174, 176, 165, 166; 24/265 B, 265 WS, 194, 196 R, 178, 24/181, 265 BC; 368/281, 282, 283; D10/32, 30, 38; 63/3, 3.1, 21, 5.1; D11/3
See application file for complete search history.

(56) References Cited

U.S. PATENT DOCUMENTS

| | | | | |
|---|---|---|---|---|
| 2,604,632 A * | 7/1952 | Whitehouse | ..................... | 2/322 |
| 2,867,023 A * | 1/1959 | Putnam | ...................... | 24/163 R |
| 2,986,313 A * | 5/1961 | Swecker, Jr. | .................. | 224/171 |
| 3,197,834 A * | 8/1965 | Sussman | ......................... | 24/194 |
| 3,830,414 A * | 8/1974 | Caprielian | .................... | 224/175 |
| 3,875,620 A | 4/1975 | Wells et al. | | |
| 5,501,180 A * | 3/1996 | Beere | ............................. | 119/858 |
| 6,944,916 B2 * | 9/2005 | Kawagoe | ...................... | 24/71 J |
| 2012/0110792 A1 * | 5/2012 | Granito | ..................... | 24/265 EC |

FOREIGN PATENT DOCUMENTS

| | | | |
|---|---|---|---|
| CN | 101366558 B | | 4/2011 |
| DE | 102005005834 | * | 8/2006 |
| JP | 2005-204804 A | | 8/2005 |
| JP | 2005204804 A | * | 8/2005 |

\* cited by examiner

*Primary Examiner* — Justin Larson
*Assistant Examiner* — Phillip Schmidt
(74) *Attorney, Agent, or Firm* — Global IP Counselors, LLP

(57) ABSTRACT

The band is provided with a first band member and a second band member attached to an instrument main body, and a linking member. Each of the band members is provided with an expanding section that expands along a band extension direction, the expanding section having pliability, and having first slits having a pair of slits lying along the width direction and a slit lying along the band extension direction, and a pair of second slits lying along the width direction to communicate with the outside of the expanding section. A linking member is provided with a fixed member; a sliding member capable of sliding along the band extension direction of the first band member and provided with a linking section (projecting rod) for linking with the second band member; and an urging member for urging the sliding member in the opposite direction from the band extension direction.

12 Claims, 13 Drawing Sheets

BAND AND ELECTRONIC INSTRUMENT

CROSS-REFERENCE TO RELATED APPLICATIONS

This application claims priority to Japanese Patent Application No. 2010-221340 filed on Sep. 30, 2010. The entire disclosure of Japanese Patent Application No. 2010-221340 is hereby incorporated herein by reference.

BACKGROUND

1. Technological Field

The present invention relates to a band for attaching the instrument body of a watch or an electronic instrument for measuring biological information to the wrist, etc., of a wearer; and to an electronic instrument provided with the band.

2. Background Technology

Measurement devices intended to be worn on the wrist, etc., of a wearer in order to measure biological information such as pulse, wristwatches having functions for measuring such biological information, and similar electronic instruments are known. With such electronic instruments, it is necessary for the instrument main body, which carries out the measurements, to be positioned in intimate contact against the proper region of in the body, such as the wrist, etc. A belt attached to the instrument main body and designed to expand is known in the art (for example, see Patent Citation 1).

The biological information measurement device of Patent Citation 1 is provided with a device main body positioned in intimate contact against the wrist; a band having a first band and a second band attached to either edge of the device main body; and a cover member. Of these components, the first band and the second band are provided, in order from the device main body side, with a link section, an expanding section, and a main section. When the device main body is attached to the wrist, the expanding sections expand along the lengthwise section of each band. The cover member is provided with a guide section positioned at the back side (the side facing the wrist) of the expanding section, and the guide section guides expansion of the band in the lengthwise direction.

When a biological information measurement device of this sort is worn on the wrist, tensile force is exerted on the band through operation by the wearer, and the device main body is worn on the wrist in a state in which the expanding sections are expanded by this tensile force. When the wearer subsequently releases the hand from the band, recovery force is exerted on the expanding sections. In so doing, the band retightens to bring the device main body into intimate contact against the wrist, irrespective of the extent of tightening of the device main body onto the wrist by the wearer.

In Patent Citation 1, by way of exemplary expanding sections, there are shown sections of elastic material such as rubber sewn to a mesh pattern, as well as a expandable metal bridge provided with a first bridge member, a second bridge member, and a coil spring; a resin bridge; and a region of undulating profile formed from urethane.

Japanese Patent Application Publication No. 2005-204804 (Patent Citation 1) is an example of the related art.

SUMMARY

Problems to Be Solved by the Invention

However, with the biological information measurement device disclosed in the above-described Patent Citation 1, because expansion of the band from the device main body is guided by the guide section, a problem arises in that it is difficult to attach the device main body to the wrist with the proper orientation. Specifically, due to individual differences in the contours of the wrist, if expansion is permitted only in the expansion portions while twist of the expanding portions relative to the device main body is not permitted as with the band disclosed in Patent Citation 1, there will be cases where the device main body is worn the wrist in an inclined state. In such cases, the problem of reduced accuracy of measurement of biological information may arise.

One of the advantages of the invention is to provide a band and an electronic instrument whereby an instrument main body is properly attachable to the body.

Means Used to Solve the Above-Mentioned Problems

The band of the invention is a band for attaching an instrument main body of an electronic instrument to the body, characterized by including a first band member and a second band member respectively attached to the instrument main body; and a linking member provided to the first band member at an end opposite from the instrument main body, the linking member adapted for linking together the first band member and the second band member; wherein each of the first band member and the second band member is provided with an expanding section that expands along a band extension direction coincident with the direction of extension thereof from the instrument main body; the expanding section is formed of material having pliability; the expanding section has first slits having a pair of slits lying along the width direction of the band member and a slit lying along the band extension direction and connecting the pair of slits, and a pair of second slits formed in locations sandwiched between the pair of slits and lying along the width direction of the band member to communicate with the outside of the expanding section; the linking member is provided with a fixed member fixed to the first band member, a sliding member slidably furnished relative to the fixed member along the band extension direction of the first band member, and an urging member disposed between the fixed member and the sliding member, the urging member adapted for urging the sliding member in the opposite direction from the band extension direction of the first band member; and the sliding member is provided with a linking section for linking with the second band member.

According to the invention, the first band member and the second band member are provided with expanding sections having pliability. These expanding sections have first slits and second slits, whereby in the expanding sections there is permitted planar twisting such that the gap (gap in the band extension direction) of one of the second slits expands while the gap of the other second slit contracts. Also, because of the expanding sections, rotation about a center axis coincident with the band extension direction of the first band member and the second band member (three-dimensional twisting) is permitted as well. Because of these expanding sections, incline of the instrument main body and the band members can be absorbed, whereby the instrument main body can be worn properly depending on the contours of the region of the body where the instrument main body is worn.

Also, because the expanding sections have first slits and second slits, expansion of the band members along the band extension direction is permitted. Because of this, retightening of the band can be carried out during linking of the first band member and the second band member by the linking member. Consequently, the instrument main body can be brought into more intimate contact against the body.

Further, the sliding member undergoes sliding travel along the band extension direction of the first band member relative to the fixed member which is fixed to the first band member, while the urging member disposed between the fixed member and the sliding member urges the sliding member in opposite direction from the band extension direction. In so doing, the sliding member, which experienced sliding during linking of the first band member and the second band member by the linking member, attempts to return under the urging force of the urging member, and therefore retightening of the band can be carried out together with the above-described expanding sections. Consequently, the instrument main body can be pressed against the body with proper pressure, and the tightening force of the band can be adjusted to and maintained at proper magnitude.

With this band, when the band is worn on the wrist etc., three-dimensional movement of the instrument main body (include of the instrument main body and the band) can be absorbed through twisting of the expanding sections if necessary. Also, through contraction of the expanding sections and the linking member once worn, the instrument main body can be reliably brought into intimate contact against the body with proper tightening force.

In particular, if the expanding section in each band member is formed in proximity to the end lying towards the instrument main body, when the band is worn on the wrist, the expanding sections will be disposed at symmetric positions to either side of the instrument main body, with the linking member positioned to the opposite side from the instrument main body. Because of this, the band members can exert uniform tensile force on the instrument main body contacting the body. Consequently, the instrument main body can be horizontally stabilized in intimate contact against the wrist.

According to the invention, in preferred practice, the expanding section has a first connecting section positioned to the instrument main body side, a second connecting section positioned to the opposite side from the instrument main body side, and a first U-shaped section and a second U-shaped section respectively connected by the first connecting section and the second connecting section; each of the first connecting section and the second connecting section has a basal section lying along the width direction of the band member having the expanding section, and a pair of extending sections extending along the band extension direction of the band member from either end of the basal section; the first U-shaped section and the second U-shaped section are disposed across a predetermined gap such that the bottom sections of the respective U shapes are in mutual opposition; of the respective pairs of extending sections of the first connecting section and the second connecting section, the extending sections situated towards one end in the width direction of the band member connect respectively to a distal end of the U shape in the U-shaped section that, of the first U-shaped section and the second U-shaped section, is the section situated towards the one end, while the extending sections situated towards another end connect respectively to a distal end of the U shape in the U-shaped section that, of the first U-shaped section and the second U-shaped section, is the section situated towards the another end; the first slits are formed between the first connecting section and the second connecting section, and between the first U-shaped section and the second U-shaped section; and the second slits are formed between the distal ends of the first U-shaped section and between the distal ends of the second U-shaped section.

It is not necessary for the contours of the first U-shaped section and the second U-shaped section to be strictly U-shaped, and contours approximating a C shape are included herein as well.

According to the invention, the above-described first slits and second slits are formed in the expanding sections by combining the first connecting section and the second connecting section, as well as the first U-shaped section and the second U-shaped section, in the aforedescribed manner. In so doing, the first slits and second slits can be formed in the expanding sections in a reliable manner; and expansion along the band extension direction and the above-described twisting can be reliably permitted to take place in the expanding sections by exertion of stress on these expanding sections. Consequently, the instrument main body can be brought into intimate contact against the body in a reliable manner.

In the invention, in preferred practice, the fixed member has an indicator section for indicating the amount by which the sliding member slides.

Graduations and markings can be given as examples of arrangements for indicating the amount of slide of the sliding member.

According to the invention, because the amount of slide of the sliding member can be verified with the indicator section, the proper level of tensile force can be exerted on the band, and using the amount of slide as a guide, it can be verified that the instrument main body is being worn against the body with the proper pressure.

In the invention, in preferred practice, either the fixed member or the sliding member has a protruding section formed along the sliding direction of sliding member, while the other has a recessed section that mates with the protruding section.

According to the invention, because sliding of the sliding member is guided by the protruding section and recessed section combined together, the sliding member can be made to slide in stable fashion. Also, twisting and travel of the sliding member along the width direction of the first band member can be restricted by these arrangements, whereby the strength of the linking member can be enhanced.

In the invention, in preferred practice, the linking section is a projecting rod for passing through a hole formed in the second band member; and the sliding member is provided with uplifting sections positioned towards the first band member side relative to the projecting rod, the uplifting sections adapted for uplifting the second band member having the projecting rod passed through the hole.

According to the invention, the excess portion of the second band member (the portion of the second band member lying toward the distal end in the band extension direction from the hole through which the projecting rod has passed) is uplifted in a direction away from the first band member by the uplifting sections. In so doing, the planar area of contact between the first band member and the second band member can be smaller, whereby hindered sliding of the sliding member caused by contact by these band members can be minimized. Consequently, sliding of the sliding member can be carried out reliably.

In the invention, in preferred practice, the first band member is provided with a band guide for disposing, along the first band member, the end section of the second band member in the band extension direction of the second band member; the band guide is provided with a main section attached to the first band member, and a pipe rotatably furnished to the main section; the main section has an restraining section lying along the width direction of the first band member, and curving sections that respectively curve in the same direction from either end of the restraining section; with the band guide attached to the first band member, an opening section through which the second band member is inserted is formed by the first band member and the main section; and the pipe is rotatably furnished to the restraining section, such that an axis of rotation of the pipe lies along the width direction of the first band member.

According to the invention, a pipe is rotatably furnished to the restraining section which forms an edge of the opening section for insertion of the second band member. In so doing, frictional resistance between the band guide and the second band member which has been inserted into the opening section can be reduced. Consequently, sliding resistance of the sliding member which is linked to the second band member via the linking section can be reduced, and sliding of the sliding member can be carried out more reliably.

In the invention, in preferred practice, the first band member has a thick section; and holes into which the distal ends of the curving sections are inserted are formed on side faces lying along the band extension direction of the first band member in the thick section and orthogonal to the width direction of the first band member.

According to the invention, holes into which the distal ends of the curving sections are inserted are formed on side faces of the thick section of the first band member, specifically, on side faces that do not contact the body. In so doing, direct contact of the band guide with the body can be prevented. Consequently, unwanted application of pressure to the body by the band guide can be prevented.

The electronic instrument of the invention is characterized by including an instrument main body for contacting the body and measuring biological information; and the aforementioned band, attached to the instrument main body.

According to the invention, effects comparable to the above-described bands are produced, and therefore measurement of biological information by the instrument main body can be carried out in a stable manner, and the accuracy of measurement can be improved.

Effect of the Invention

According to the invention, twisting (inclination) between the instrument main body and the band members during wear of the electronic instrument on the body can be absorbed by the expanding sections. Also, because the sliding member which slides relative to the fixed member is urged by the urging member in the opposite direction from the band extension direction of the first band member, retightening of the band together with the expanding sections can be carried out during wear of the electronic instrument on the body. Consequently, the electronic instrument can be worn properly on the body.

BRIEF DESCRIPTION OF THE DRAWINGS

Referring now to the attached drawings which form a part of this original disclosure.

DETAILED DESCRIPTION OF EXEMPLARY EMBODIMENTS

An embodiment of the invention is described below based on the drawings.

General Configuration of Biological Information Measurement Device

Figure 1:
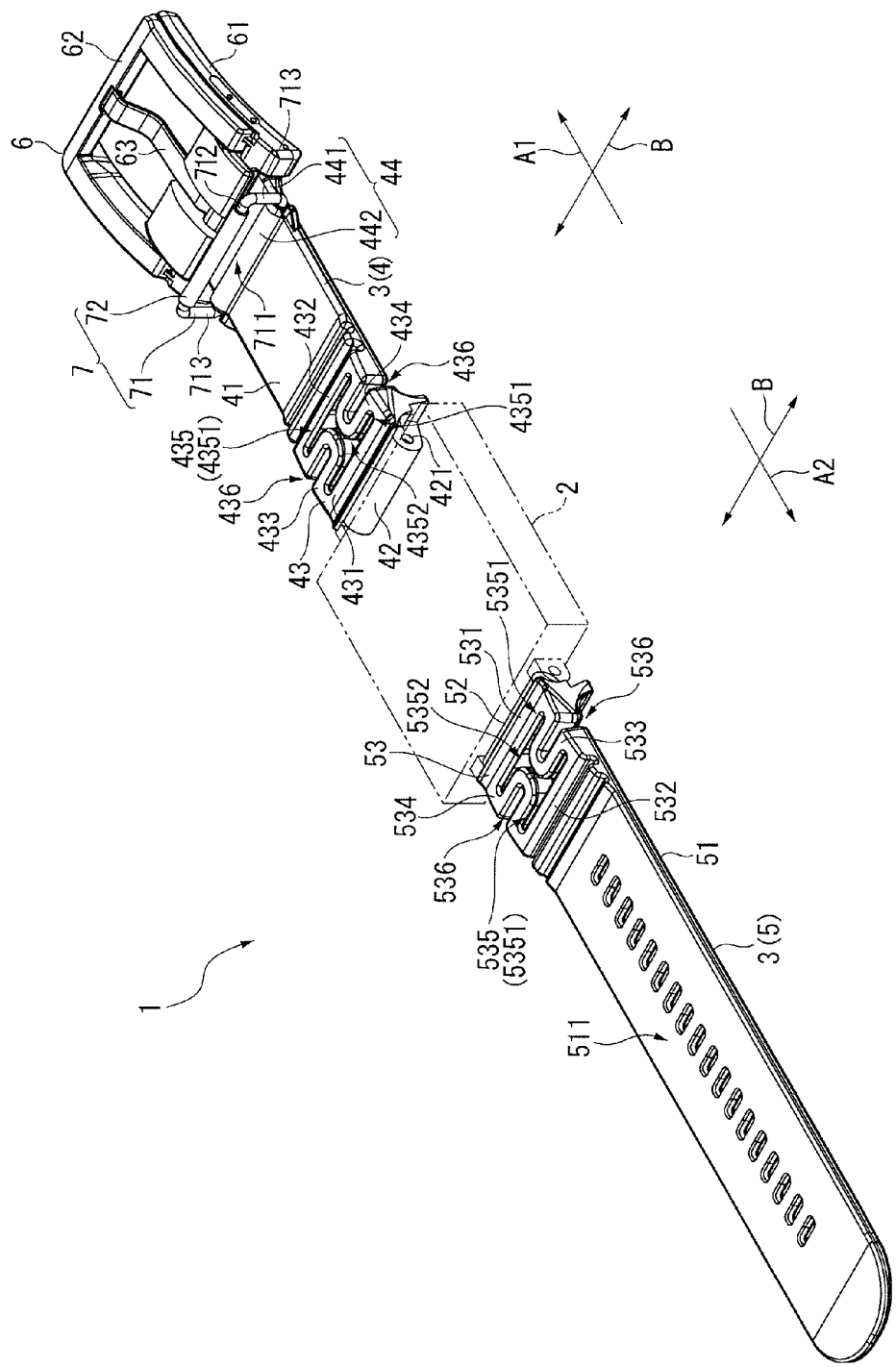
FIG. 1 is a perspective view depicting a biological information measurement device according to an embodiment of the invention.

FIG. 1 is a perspective view depicting a biological information measurement device 1 according to an embodiment of the invention.

The biological information measurement device 1 according to the present embodiment is an electronic instrument intended for wear on the body, e.g., the wrist, to measure biological information such as the pulse. As depicted in FIG. 1, this biological information measurement device 1 has an instrument main body 2 to be placed in intimate contact with the body to measure biological information, and a band 3 attached to the instrument main body 2.

Herein, lugs (not shown) for respective attachment of a first band member 4 and a second band member 5 constituting the band 3 are formed at either end of the instrument main body 2.

Configuration of Band

The purpose of the band 3 is for wear of the instrument main body 2 on the body. This band 3 is provided with a first band member 4 attached to lugs of the instrument main body 2 (expressed in terms of the clock, lugs at the 12:00 side), a second band member 5 attached to lugs (expressed in terms of the clock, lugs at the 6:00 side), a linking member 6 for linking the first band member 4 and the second band member 5, and a band guide 7 for disposing the second band member 5 along the first band member 4.

Below, in the first band member 4, the side towards the instrument main body 2 is described as "one end," and the side towards the linking member 6 as the "other end." Likewise, in the second band member 5, the side towards the instrument main body 2 is described as "one end," and the side opposite from the instrument main body 2 side as the "other end."

Configuration of First Band Member

The first band member 4 is an integrally molded part of flat oblong shape formed of urethane or silicone material. The first band member 4 has a band main body 41, a first linking section 42 and an expanding section 43 formed at one end (the instrument main body 2 side) of the band main body 41, and a second linking section 44 formed at the other end of the band main body 41.

The first linking section 42 has a hole section 421 for passage of a spring rod (not shown) attached to the above-described lugs, and the first linking section 42 is attached to the instrument main body 2 via this spring rod.

Figure 2:
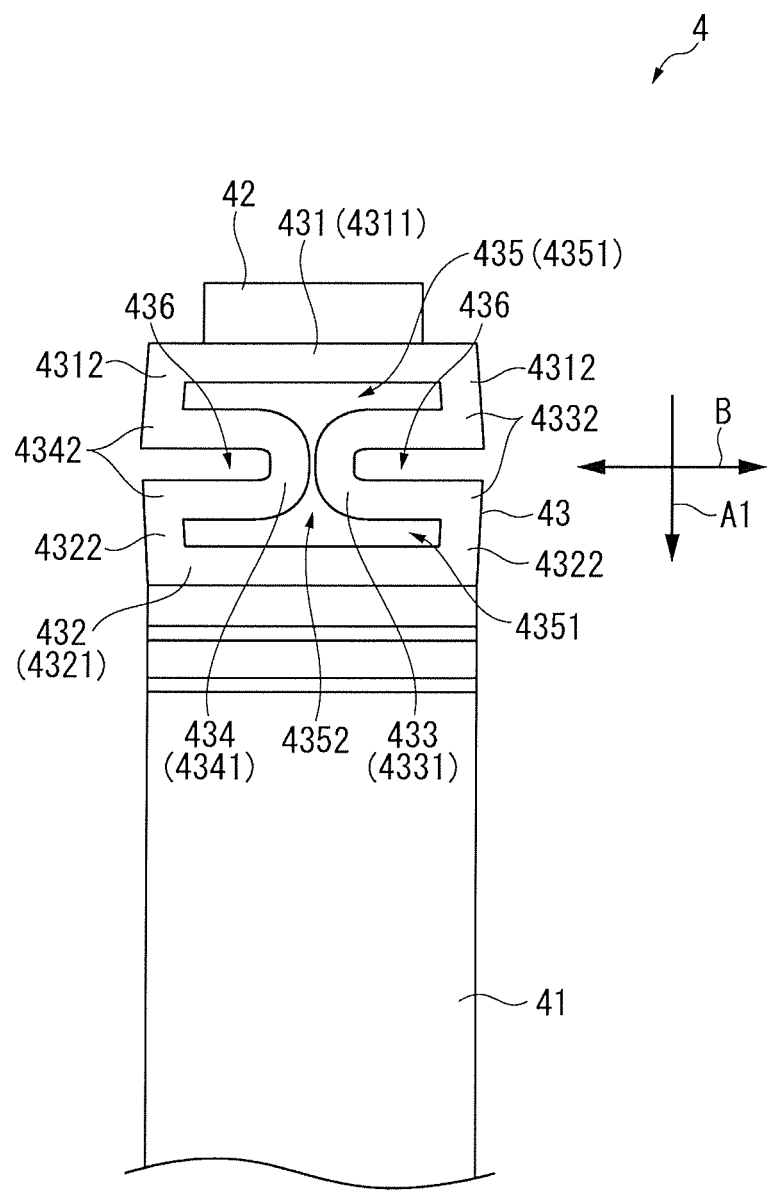
FIG. 2 is a plan view depicting an expanding section in the embodiment.

FIG. 2 is a plan view depicting the expanding section 43.

The expanding section 43 is positioned to the other end with respect to the first linking section 42, and positioned in the band 3 in proximity to the instrument main body 2. This expanding section 43 has pliability, and is formed with greater thickness than the band main body 41 in order to ensure strength during expansion/contraction and flexure. As depicted in FIGS. 1 and 2, this expanding section 43 has a first connecting section 431 and a second connecting section 432, as well as U-shaped sections 433, 434 which are connect respectively thereby and which are approximately U-shaped in plan view.

The first connecting section 431 and the second connecting section 432 are respectively formed in the expanding section 43 at one end and the other end thereof.

The first connecting section 431 has a basal section 4311 and a pair of extending sections 4312.

The basal section 4311 is formed along the width direction of the first band member 4 (direction B in FIGS. 1 and 2; this convention is used throughout). This basal section 4311 is connected to the first linking section 42.

The pair of extending sections 4312 are respectively formed extending out from either end of the basal section 4311 along the extension direction of the first band member 4 from the instrument main body 2 (the band extension direction of the first band member 4, or direction A1 in FIGS. 1 and 2; this convention is used throughout.)

Likewise, the second connecting section 432 has a basal section 4321 lying along direction B, and a pair of extending sections 4322 extending towards the opposite direction from direction A1, from either end of the basal section 4321.

The U-shaped sections 433, 434 are formed to approximately U shape in plan view between the first connecting section 431 and the second connecting section 432, and respectively connect with the first connecting section 431 and the second connecting section 432.

The U-shaped section 433 has a bottom section 4331 corresponding to a bottom section of U shape, and a pair of extending sections 4332 respectively extending in the same direction from either end of the bottom section 4331. Like the U-shaped section 433, the U-shaped section 434 has a bottom section 4341 and a pair of extending sections 4342.

These U-shaped sections 433, 434 are formed such that their respective bottom sections 4331, 4341 face towards one another, with the bottom sections 4331, 4341 lying in direction A1, while the extending sections 4332, 4342 are respectively formed along direction B. These U-shaped sections 433, 434 correspond to the first U-shaped section and the second U-shaped section of the invention.

In this expanding section 43, of the pairs of extending sections 4312, 4322, the distal ends positioned at one end in direction B (the right side in FIG. 2) of the extending sections 4312, 4322 are respectively connected to the distal ends of the pair of extending sections 4332 in the U-shaped section 433.

Likewise, of the pairs of extending sections 4312, 4322, the distal ends positioned at the other end in direction B (the left side in FIG. 2) of the extending sections 4312, 4322 are respectively connected to the distal ends of the pair of extending sections 4342 in the U-shaped section 434.

The connecting sections 431, 432 and the U-shaped sections 433, 434 form first slits 435 in an approximately sideways H-shaped pattern inside the expanding section 43. Second slits 436 which communicate with the outside of the expanding section 43 are formed along direction B by the inside edges of the U-shaped sections 433, 434. In other words, the second slits 436 are formed along the extending sections 4332, 4342 between the distal ends at the opposite side from the bottom sections of the U-shaped sections 433, 434.

Of these, the first slits 435 are composed of a pair of slits 4351 lying along direction B, and a slit 4352 that connects with the pair of slits 4351 and lies along direction A1. With the expanding section 43 in the unloaded state, these slits 435, 436 need not necessarily constitute gaps, and may be mere incisions instead.

Figure 3:
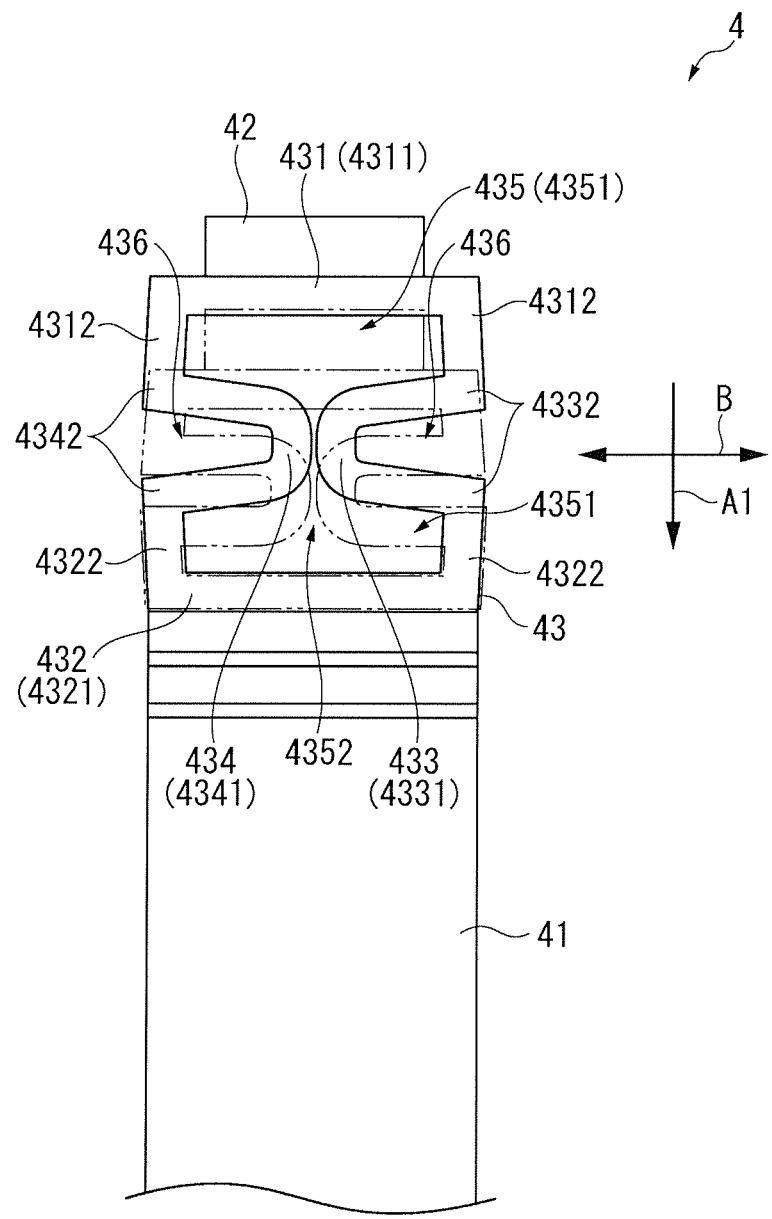
FIG. 3 is a plan view depicting an expanding section in the embodiment in a stretched state.

FIG. 3 is a plan view depicting the expanding section 43 in a stretched state.

As depicted in FIG. 3, by virtue of having the first slits 435 and the second slits 436, the expanding section 43 is able to stretch in direction A1 in response to tensile force by the wearer. At this time, the expanding section 43 experiences stretching that respectively increases the dimensions between the basal sections 4311, 4321 and the extending sections 4332, 4342, the dimension between the pair of extending sections 4332, and the dimension between the pair of extending sections 4342. In other words, the expanding section 43 experiences stretching that increases the dimensions of the slits 4351 and the second slits 436 in direction A1. Because the expanding section 43 has pliability, during stretching of the expanding section 43, recovery force towards return is exerted. Because of this, when tensile force by the wearer ceases, the section contracts in the opposite direction from direction A1 owing to the recovery force, and the expanding section 43 returns.

Figure 4:
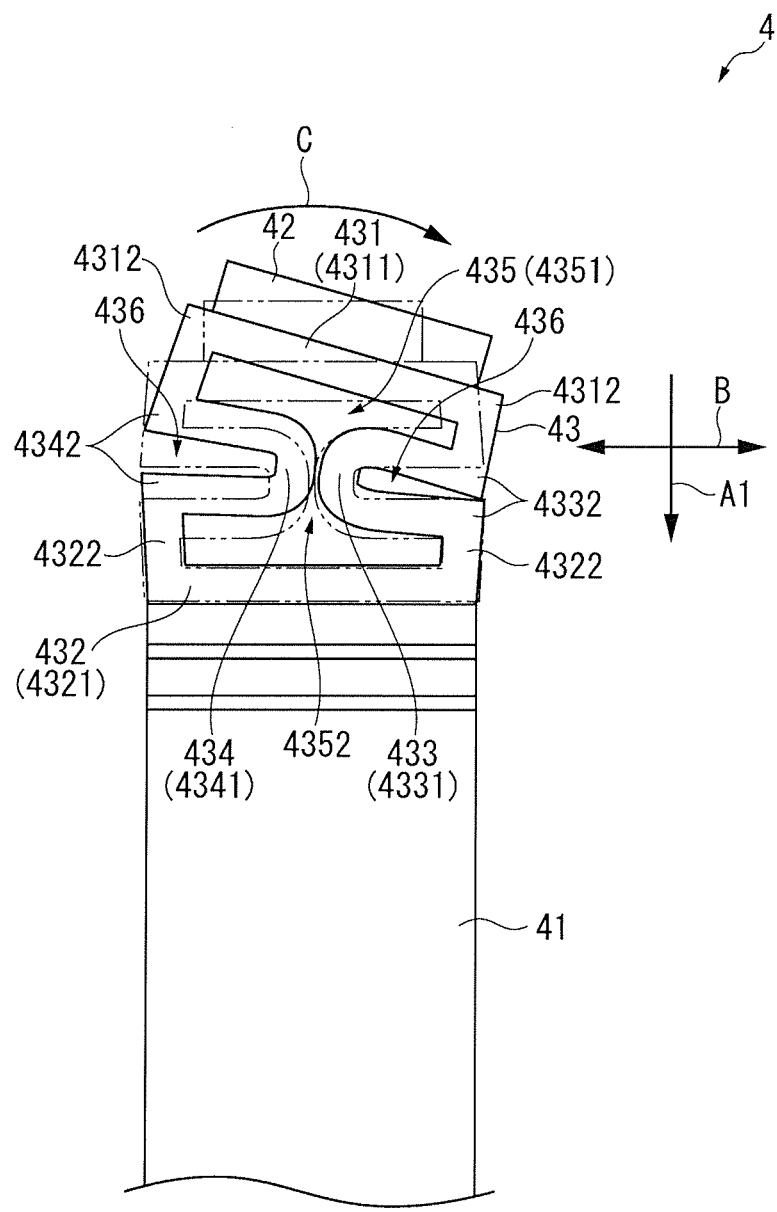
FIG. 4 is a plan view depicting an expanding section in the embodiment in a twisted state.

FIG. 4 is a plan view depicting the expanding section 43 in a twisted state.

As depicted in FIG. 4, by virtue of having the first slits 435 and the second slits 436, the expanding section 43 is able to twist. This twisting can be twisting in direction C in FIG. 4, specifically, planar twisting whereby one end in the width direction of the basal section 4311 of the first connecting section 431 (e.g., the end section at the right side in FIG. 4) moves closer to the second connecting section 432 as compared with the other end (e.g., the end section at the left side in FIG. 4); or three-dimensional twisting about a center axis in direction A1. Owing to this twistable configuration of the expanding section 43, in the case where the biological information measurement device 1 is worn on the wrist, etc., twisting (inclination) of the instrument main body 2 and the first band member 4 is permitted, and the instrument main body 2 can be properly pressed against the wrist.

Returning to FIG. 1, the second linking section 44 has a first attachment section 441 for attachment of the linking member 6, described below, and a second attachment section 442 for attachment of the band guide, 7, described below.

The first attachment section 441 has a passage hole (not shown) for passage of a spring rod 45 (see FIG. 12) along direction B. A fixed member 61, described below, is attached to the first attachment section 441 by this spring rod 45, whereby the linking member 6 is attached to the first band member 4.

The second attachment section 442 corresponds to the thick section of the invention, and is formed with greater thickness than the band main body 41 so as to protrude from the top face side of the first band member 4 (the opposite side from the side facing the body). Holes 4421 (see FIG. 12) for inserting the distal ends of curving sections 713 of the band guide 7 are formed in two side faces of this second attachment section 442 (the two side faces lying along direction A1 and approximately orthogonal to direction B in the first band member 4).

Configuration of Second Band Member

As described above, the second band member 5 is attached at one end to lugs of the instrument main body 2. Like the first band member 4, this second band member 5 is an integrally molded part of flat oblong shape formed of urethane or silicone material having pliability. This second band member 5 is provided with a band main body 51, and a linking section 52 and an expanding section 53 which are formed at the instrument main body 2 side of the band main body 51.

The band main body 51 has a plurality of holes 511 formed along the direction of extension of the second band member 5 from the instrument main body 2 (the band extension direction of the second band member 5, or direction A2 in FIG. 1; this convention is used throughout.) A projecting rod 63, described below, of the linking member 6 is passed through any of these holes 511.

The linking section 52 and the expanding section 53 have configurations comparable to those of the first linking section 42 and the expanding section 53.

Specifically, the linking section 52 is formed at one end of the second band member 5 (the end section towards the instrument main body 2). This linking section 52 has a hole (not shown) for passage of a spring rod (not shown) which is attached to the above-described lugs.

The expanding section 53 is positioned to the other end with respect to the linking section 52, and positioned in the band 3 in proximity to the instrument main body 2. This expanding section 53 has pliability, and is formed with greater thickness than the band main body 51. This expanding section 53 has a first connecting section 531, a second connecting section 532, and U-shaped sections 533, 534 formed in a comparable manner to the sections 431 to 434 of the expanding section 43. In so doing, there are formed in the expanding section 53 first slits 535 having a pair of slits 5351 lying along direction B and a slit 5352 connecting the slits 5351 along direction A2; and a pair of second slits 536 respectively formed communicating with the outside of the expanding section 53 along direction B. Owing to these first slits 535 and second slits 536, the expanding section 53 permits expansion/contraction along direction A2 and twisting, in the same manner as the expanding section 43.

Configuration of Linking Member

Figure 5:
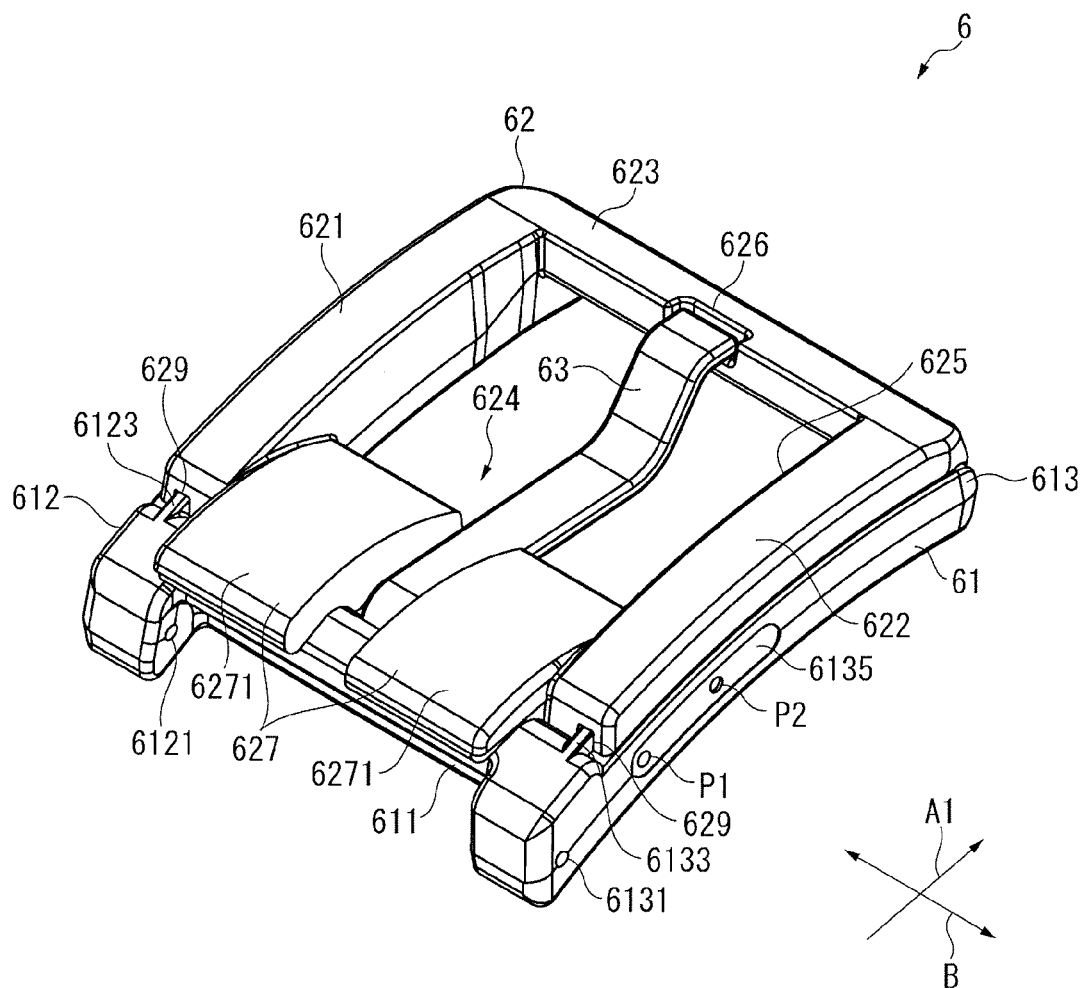
FIG. 5 is a perspective view depicting a linking member in the embodiment.
Figure 6:
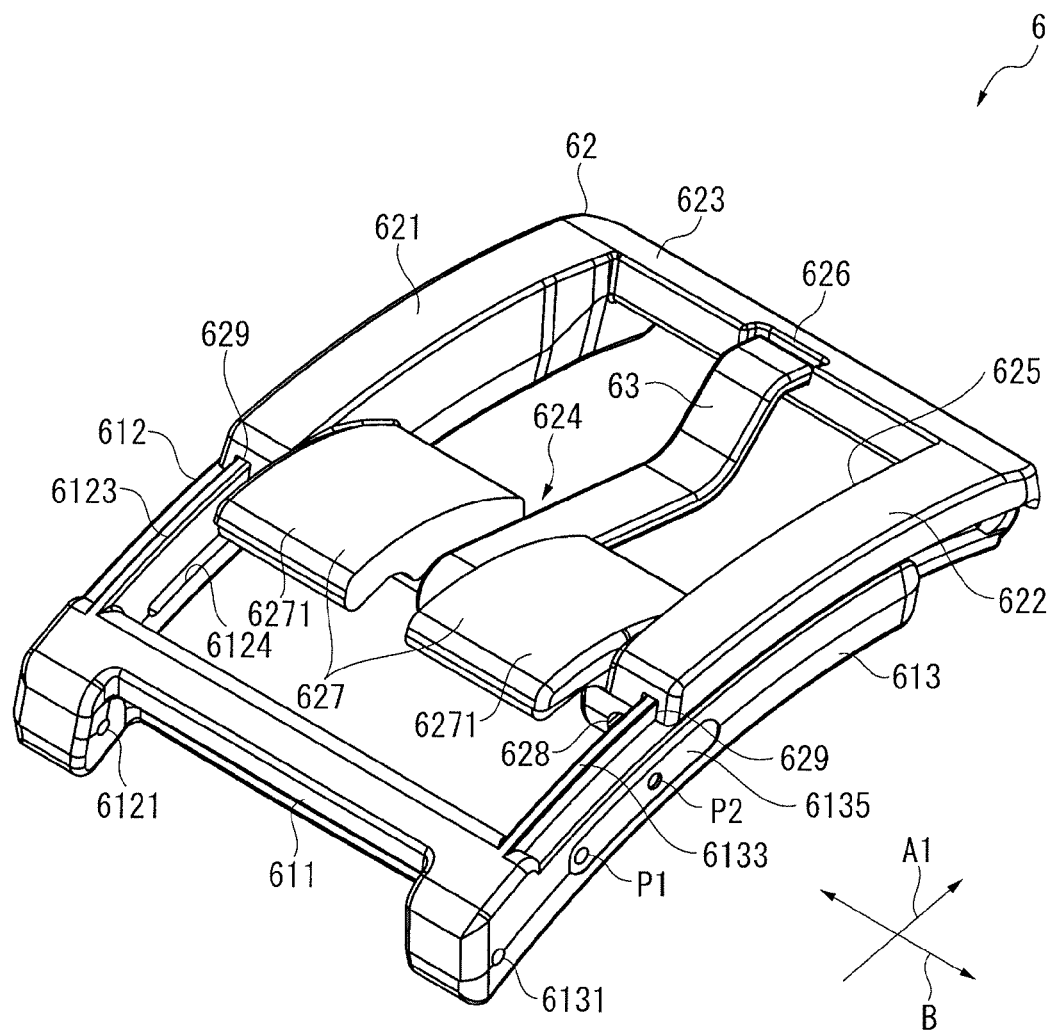
FIG. 6 is a perspective view depicting the linking member in the embodiment.
Figure 7:
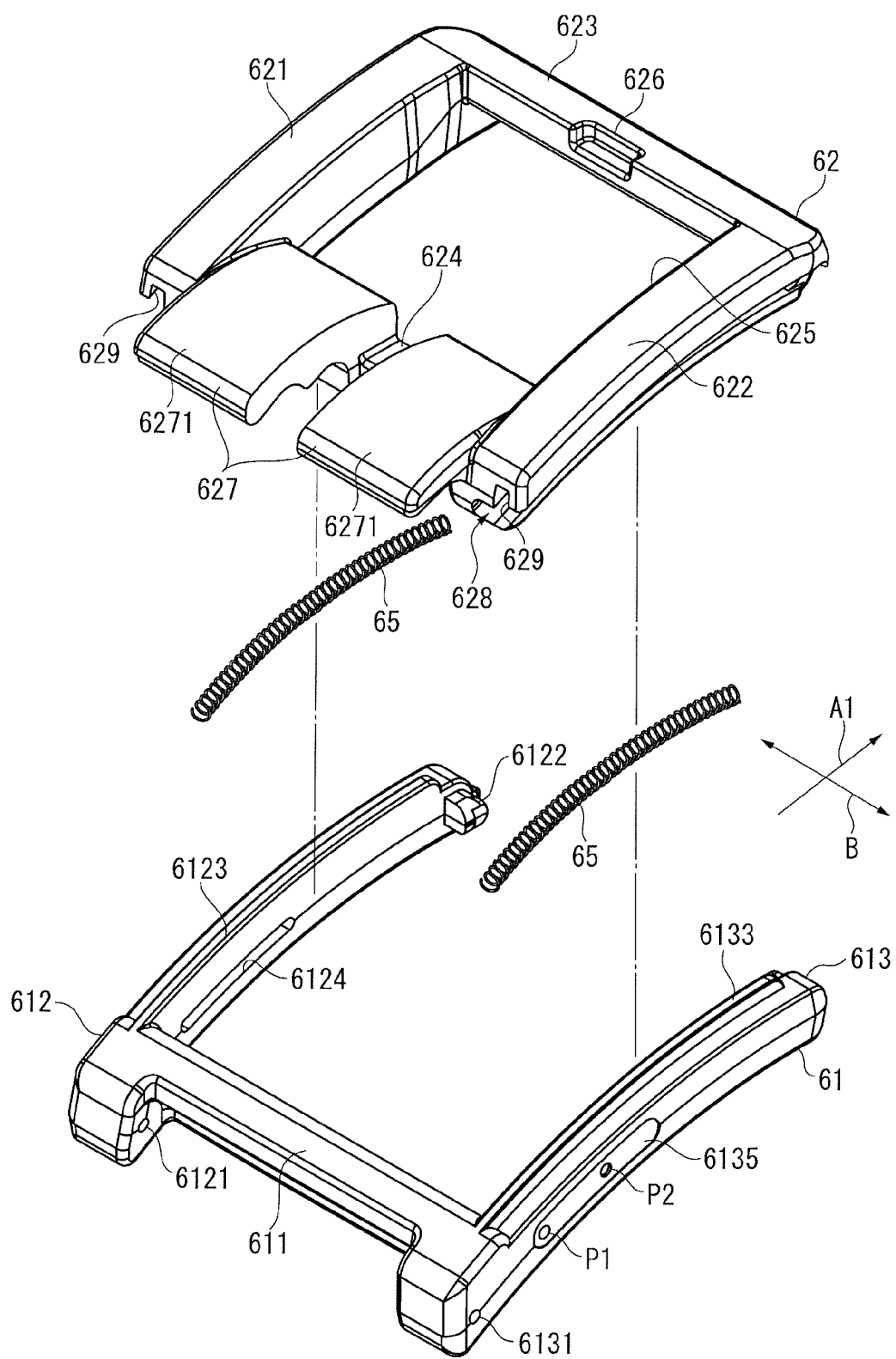
FIG. 7 is an exploded perspective view depicting the linking member in the embodiment.

FIGS. 5 and 6 are perspective views depicting the linking member 6. Of these, FIG. 5 depicts the linking member 6 prior to sliding of the sliding member 62, and FIG. 6 depicts the linking member 6 subsequent to sliding of the sliding member 62. FIG. 7 is an exploded perspective view of the linking member 6.

The linking member 6 is a member made of metal or of resin functioning as a buckle for linking the first band member 4 and the second band member 5, and is attached to the above-described first attachment section 441. As depicted in FIGS. 5 to 7, this linking member 6 is formed to arcuate shape so as to have a predetermined curvature in cross section in the thickness direction, so as to lie along the wrist.

This linking member 6 is provided with a fixed member 61 (FIGS. 5 to 7), a sliding member 62 that slides over the fixed member 61 along direction A1 (FIGS. 5 to 7), a projecting rod 63 (FIGS. 5 and 6), a spring rod 64 (FIG. 9), and coil springs 65 (FIG. 7).

Configuration of Fixed Member

As depicted in FIGS. 5 to 7, the fixed member 61 is a frame-like body that slidably supports the sliding member 62. This fixed member 61 has a basal section 611 lying along direction B, and a pair of extending sections 612, 613 connected to the basal section 611 and respectively extending out along direction A1.

The extending section 612 that is positioned to the left side in FIG. 7 has a passage hole 6121 for insertion of one end of the spring rod 45 which is passed through the above-described first attachment section 441; an engaging section 6122; a protruding section 6123; a slot 6124; and an indicator section (not shown). Because the indicator section has the same configuration as an indicator section 6135 to be described below, description is omitted here.

The engaging section 6122 is formed so as to project out from the extending section 612 at the end section thereof on the opposite side from the first band member 4 side, and towards the other extending section 613. This engaging section 6122 engages one end of the coil spring 65, described below.

The protruding section 6123 is formed along direction A1, on a top face of the extending section 612 in opposition to the sliding member 62.

The slot 6124 is formed along direction A1, on a side face of the extending section 612 in opposition to the extending section 613. The end section of the spring rod 64 described later inserts into this slot 6124.

The extending section 613 that is positioned to the right side in FIG. 7 has a passage hole 6131, an engaging section 6132 (see FIG. 9), a protruding section 6133, a slot (not shown), and an indicator section 6135 at positions symmetrical with the above-described passage hole 6121, engaging section 6122, protruding section 6123, slot 6124, and indicator section. Of these, the passage hole 6131, the engaging section 6132, the protruding section 6133, and the slot have approximately the same configuration as the sections 6121 to 6124, and therefore description is omitted.

The indicator section 6135 is formed along direction A1 on a side face of the extending section 613 on the opposite side from the extending section 612. Graduations depicting a proper sliding range of the sliding member 62 are made in this indicator section 6135. Specifically, in the present embodiment, two points P1, P2 depicting the proper sliding range are made in the indicator section 6135. As long as the end section at the first band member 4 side of the sliding member 62 is positioned within the range depicted by these two points P1, P2, a proper level of tensile force will be exerted on the band 3.

The point P1 is a hole which has been formed at the same position as the end section of the spring rod 64 (in other words, the end section on the first band member 4 side of the slot for insertion of the end section of the spring rod 64). The spring rod 64 can be removed from the slot by poking a slender rod or the like into this hole and compressing the end section of the spring rod 64, so that the linking member 6 can be disassembled.

Configuration of Sliding Member

As depicted in FIGS. 5 and 6, the sliding member 62 slides along direction A1 relative to the fixed member 61 and adjusts the length dimension of the band 3 and the pressure of the instrument main body 2 against the body. Specifically, the sliding member 62 has the function of exerting tensile force on the band 3 to bring the instrument main body 2 into intimate contact against the body.

As depicted in FIGS. 5 to 7, the sliding member 62 has a pair of first side sections 621, 622 lying along direction A1, and second side sections 623, 624 respectively connecting the end sections of the first side sections 621, 622 along direction B, thereby forming an approximately rectangular frame shape overall.

In preferred practice, the second side section 624 will be present in order to improve the strength of the sliding member 62, but the functionality of the sliding member 62 will be satisfactory even if the second side section 624 is missing.

In the approximate center of this sliding member 62 there is formed an opening 625 of approximately rectangular shape for passage of the second band member 5.

A recessed section 626 for housing the distal end of the projecting rod 63 described later is formed in the top face of the second side section 623 positioned to the opposite side from the first band member 4.

Further, a pair of uplifting sections 627 positioned so as to sandwich the projecting rod 63 described later are furnished on the top face of the second side section 624 positioned towards the first band member 4 side. These uplifting sections 627 have a sloping face 6271 of progressively greater thickness dimension towards the direction approaching the first band member 4. These uplifting sections 627 have a function of uplifting the excess portion of the second band member 5 once the projecting rod 63 has been passed through a hole 511 therein (specifically, the section to the distal end side in direction A2 from the hole 511 in the second band member 5 through which the projecting rod 63 has been passed), and preventing contact between this excess portion, the fixed member 61, and the first band member 4.

Figure 8:
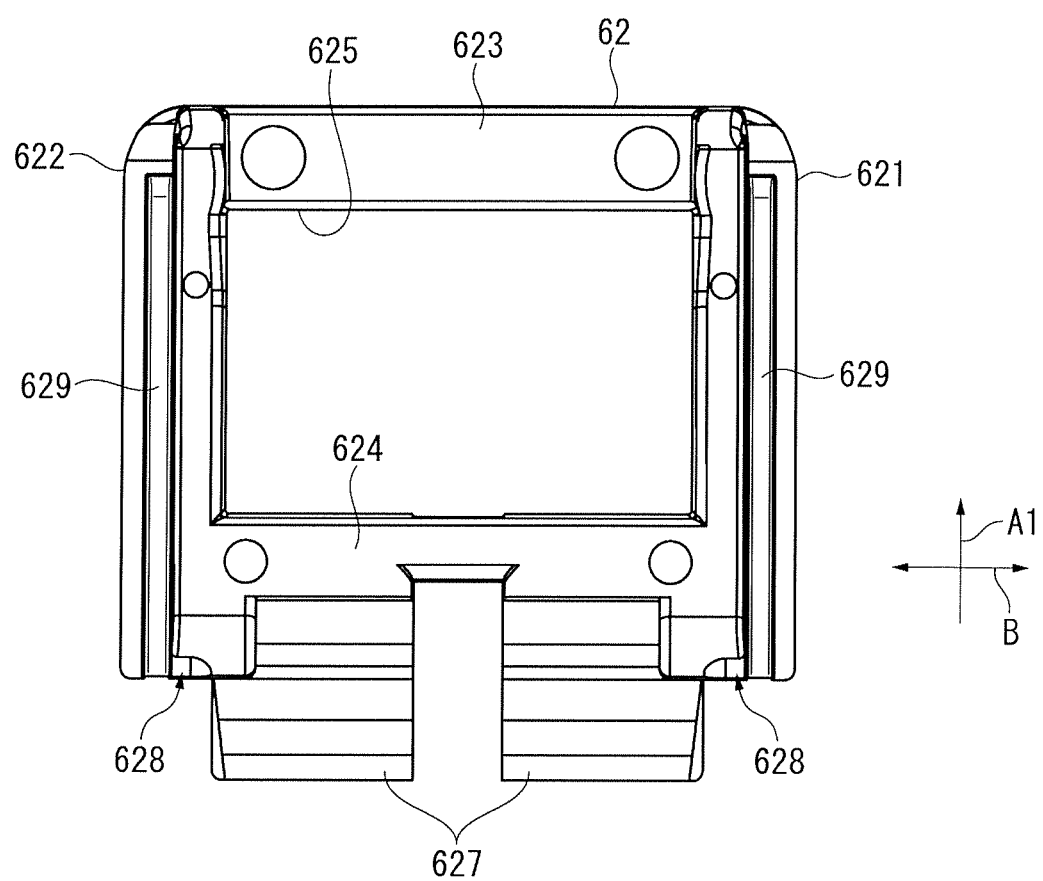
FIG. 8 is a plan view depicting the bottom face of a sliding member in the embodiment.

FIG. 8 is a plan view depicting the bottom face of the sliding member 62.

As depicted in FIG. 8, the sliding member 62 has a pair of groove sections 628 and a pair of recessed sections 629 extending along direction A1 respectively, on the outside faces of the first side sections 621, 622 and the bottom faces of the first side sections 621, 622 facing the fixed member 61.

Of these, coil springs 65 to be described later are disposed inside the groove sections 628, and the groove sections 628 are covered by the extending sections 612, 613 of the fixed member 61. At this time, the engaging sections 6122, 6132 insert within the groove sections 628.

The pair of recessed sections 629 are respectively formed to the outside of the groove sections 628. The protruding sections 6123, 6133 of the fixed member 61 fit into these recessed sections 629 when the fixed member 61 and the sliding member 62 are combined. Sliding of the sliding member 62 along direction A1 is guided thereby. By combining these recessed sections 629 and protruding sections 6123, 6133, twisting and travel in direction B by the sliding member 62 are restricted, and strength of the linking member 6 is enhanced.

Configuration of Projecting Rod

Figure 9:
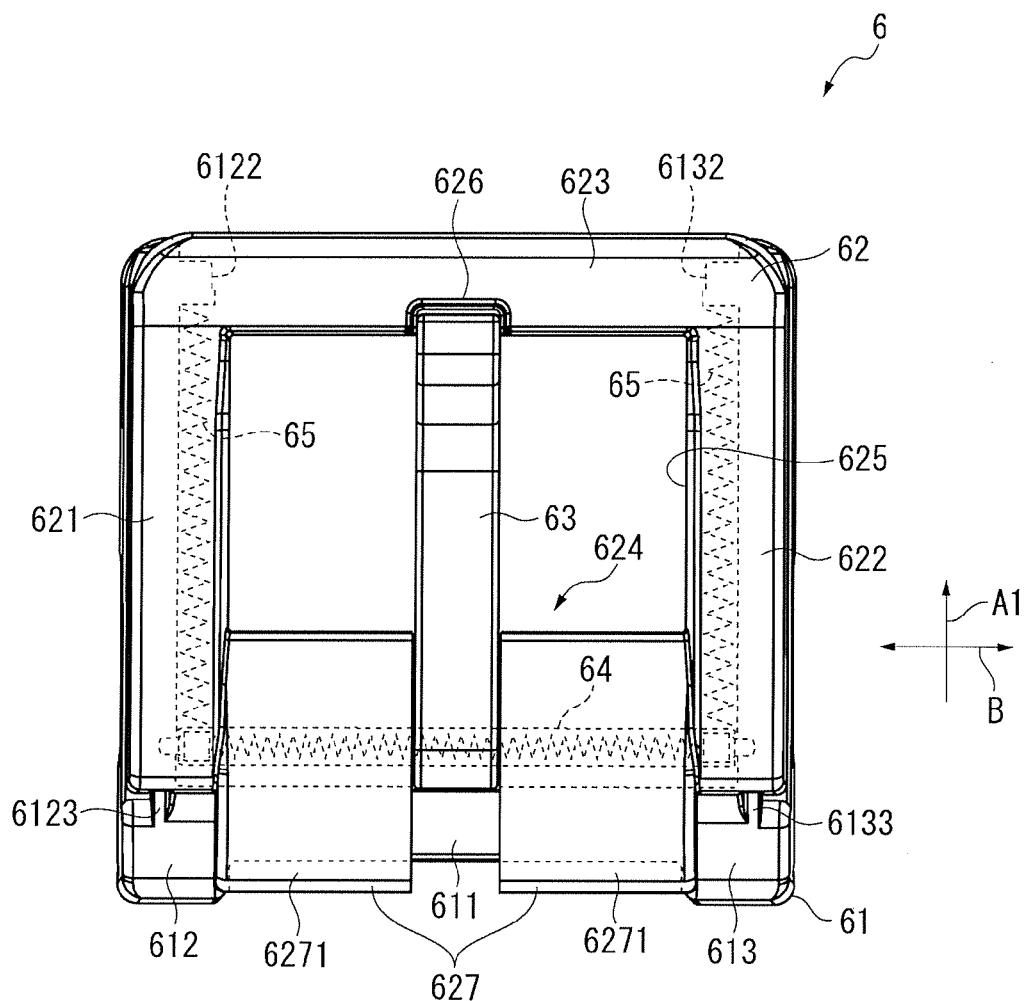
FIG. 9 is a plan view of the linking member in the embodiment, depicting positions of a projecting rod, a spring rod, and coil springs.

FIG. 9 is a plan view depicting the linking member 6. In other words, FIG. 9 is a plan view of the linking member depicting positions of the projecting rod 63, the spring rod 64, and the coil springs 65.

The projecting rod 63 corresponds to the linking section of the invention, and is adapted to insert into a hole 511 of the second band member 5 and link with the second band member 5. As depicted in FIG. 9, this projecting rod 63 is disposed so as to bridge between the recessed section 626 and a point between the pair of uplifting sections 627, and is rotatably supported by the spring rod 64. The projecting rod 63 is thereby pivotably supported on the sliding member 62.

Configuration of Spring Rod

The spring rod 64 passes along direction B through the projecting rod 63, and the two ends thereof perforate the first side sections 621, 622. Then, when the fixed member 61 and the sliding member 62 are combined, the two ends of the spring rod 64 are inserted into the slot 6124 of the extending section 612 and the slot of the extending section 613. Meanwhile, at the distal end side of the linking member 6 in direction A1, the engaging sections 6122, 6132 are inserted within the pair of groove sections 628 as described previously. Upward dislodgement of the sliding member 62 from the fixed member 61 is restricted thereby.

In this state, as the sliding member 62 slides in direction A1 while guided by the protruding sections 6123, 6133 and the recessed sections 629, the spring rod 64 slides in direction A1 within the slot together with the sliding member 62.

Configuration of Coil Springs

The coil springs 65 correspond to the urging member of the invention, and are adapted to urge the sliding member 62 in a direction approaching the first band member 4 (the opposite direction from direction A1) with respect to the fixed member 61.

As depicted in FIGS. 7 and 9, a pair of coil springs 65 are furnished along direction A1. As described previously, these coil springs 65 are respectively housed inside the groove sections 628, with one end on the first band member 4 side engaged by the end section of the spring rod 64, and the other end engaged by the engaging sections 6122, 6132.

Figure 10:
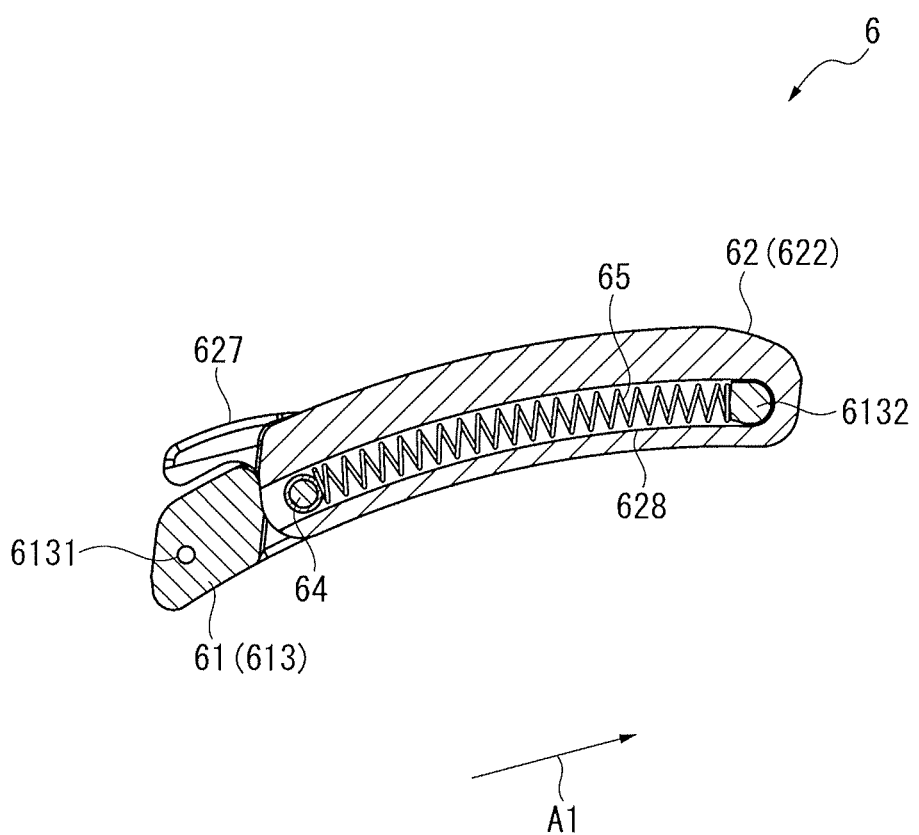
FIG. 10 is a sectional view of the linking member in the embodiment.
Figure 11:
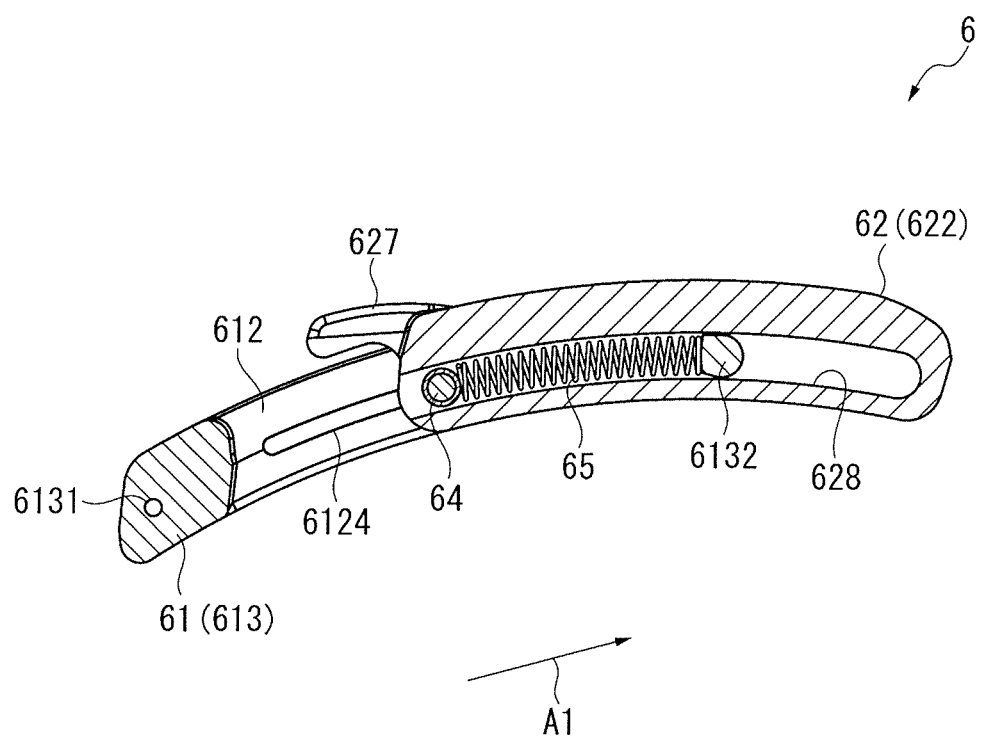
FIG. 11 is a sectional view of the linking member in the embodiment.

FIG. 10 is a sectional view of the linking member 6 depicting the state of the coil springs 65 prior to sliding of the sliding member 62, and FIG. 11 is a sectional view of the linking member 6 depicting the state of the coil springs 65 subsequent to sliding of the sliding member 62 in a first direction. FIGS. 10 and 11 are drawings showing a cross section of the linking member 6 in the extending section 613 and the first side section 622, viewed from the extending section 613 and the first side section 622 side.

In a state without sliding of the sliding member 62 (the state depicted in FIG. 5), the coil springs 65 are housed inside the groove sections 628 in state of being slightly compacted by the engaging sections 6122, 6132 (only the engaging section 6132 is illustrated in FIG. 10) and the end sections of the spring rod 64. Consequently, in this state as well, urging force for maintaining this state, specifically, urging force for urging the sliding member 62 towards the first band member 4 side, is exerted on the sliding member 62.

From this state, when the sliding member 62 now slides in direction A1 (the state depicted in FIG. 6), the coil springs 65 are compressed by the engaging sections 6122, 6132 (only the engaging section 6132 is illustrated in FIG. 11) and the spring rod 64 which slides inside the slot 6124 in association with sliding of the sliding member 62, as depicted in FIG. 11. Here, because the engaging sections 6122, 6132 are fixed, a high level of the above-described urging force is exerted on the sliding member 62, prompting the sliding member 62 to return to the state depicted in FIG. 10.

Because of this, when the band members 4, 5 are linked via the linking member 6, once the wearer releases the hand from these band members 4, 5, the sliding member 62 which previously slid in direction A1 due to tensile force of the wearer now slides in the opposite direction from direction A1 due to tensile force of the coil spring 65. Because of this, the second band member 5 which was linked by the projecting rod 63 is drawn along the first band member 4 in the opposite direction from direction A1, whereby the band 3 retightens in response to pressure of the instrument main body 2 against the body. Consequently, the instrument main body 2 is brought into intimate contact against the body at proper pressure.

Configuration of Band Guide

The band guide 7 is a member for disposing the excess portion of the second band member 5 along the first band member 4, and the member functions like the fixed ring of the band of a wristwatch. As depicted in FIG. 1, this band guide 7 has a main body section 71 attached to the second attachment section 442 of the first band member 4, and a pipe 72 rotatably furnished to the main body section 71.

The main body section 71 is provided with an restraining section 712 lying along direction B, and a pair of curving sections 713 that respectively curve in the same direction from either end of the restraining section 712. When this main body section 71 is then attached to the first band member 4, an opening 711 for the second band member 5 to pass through is formed by the main body section 71 and the first band member 4.

Figure 12:
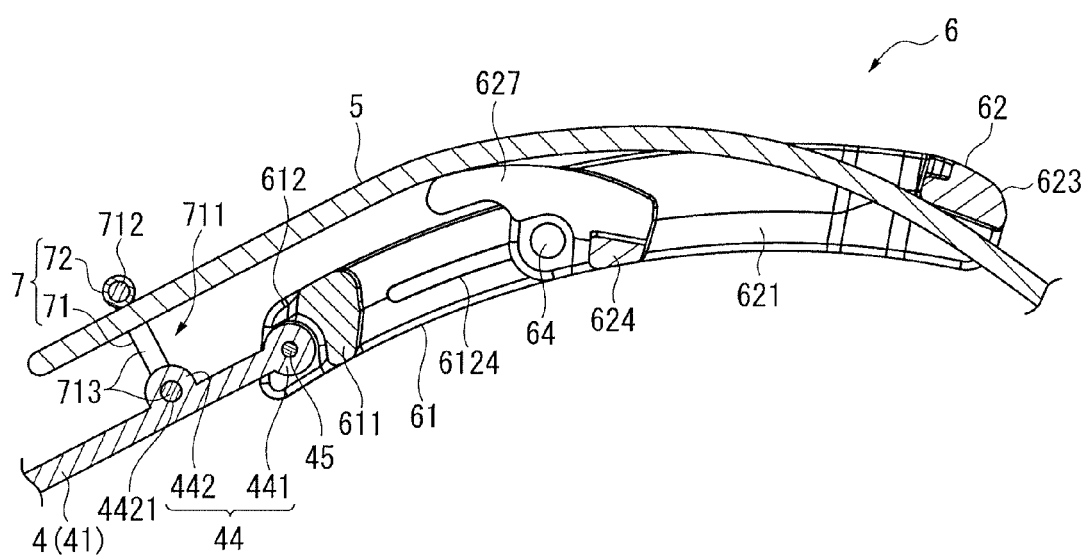
FIG. 12 is a sectional view of a band depicting the band guide and the second band member in a mated state.

Of these, the distal ends of the curving sections 713 further curve in a direction closer to one another, and are inserted into the holes 4421 formed in either side face of the second attachment section 442 (see FIG. 12).

FIG. 12 is a sectional view of the band 3 depicting the band guide 7 and the second band member 5 in a mated state.

The pipe 72 is attached to the restraining section 712 such that the rotation axis lies along the axial direction of the restraining section 712. Specifically, the restraining section 712 is covered by the pipe 71. As depicted in FIG. 12, this pipe 72 contacts the second band member 5 inserted into the opening 711, and then rotates as the second band member 5 is inserted further in. Because of this, frictional resistance between the pipe 72 and the second band member 5 is reduced, and the band member 5 can be inserted easily into the opening 711. Also, by reducing the frictional resistance, the second band member 5 is not engaged by the band guide 7, and therefore sliding of the above-described sliding member 62 can be carried out easily. At this time, because the above-described uplifting sections 627 uplift the second band member 5 to avoid contact thereof with the first band member 4, sliding of the sliding member 62 may be carried out more smoothly.

Differences from Ordinary Band for a Wristwatch

Pulse measurements were carried out using the biological information measurement device 1 according to the present embodiment and a biological information measurement device provided with an ordinary band for a wristwatch in place of the band 3, and the respective MN ratios were compared. The pulse measurements were carried out on ten test subjects using the same biological information measurement device, while exchanging the band only; and the MN ratios obtained using the respective bands were compared.

Here, MN ratio indicates a value obtained by measuring pulse-induced changes in light reflected by contraction and expansion of blood vessels when light is directed onto the surface of the body, measuring the changes as voltage and dividing the "power pulse frequency" by "the maximum value of power of other (noise)" in the data. Higher values can be said to represent pure pulse data with minimal noise, and the data may be deemed reliable.

Figure 13:
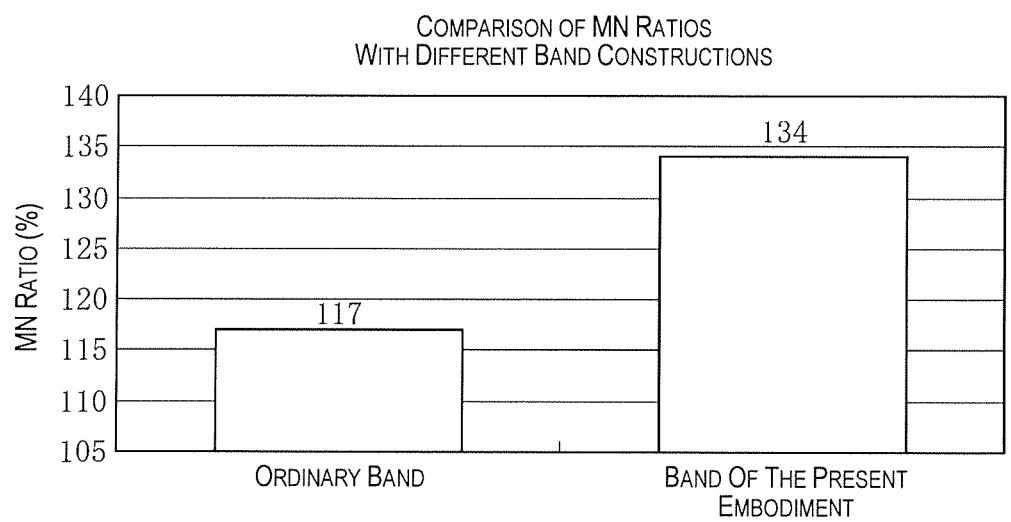
FIG. 13 is a diagram depicting MN ratios obtained by carrying out pulse measurements using the biological information measurement device in the embodiment, and a biological information measurement device provided with an ordinary wristwatch band.

FIG. 13 is a diagram depicting MN ratios obtained by carrying out pulse measurements using the biological information measurement device 1 according to the embodiment, and the biological information measurement device provided with an ordinary wristwatch band in place of the band 3.

As depicted in FIG. 13, with the biological information measurement device employing an ordinary wristwatch band (a urethane band), the MN ratio was 117%. In contrast to this, with the biological information measurement device 1 provided with the band 3, the MN ratio improved to 134%. Consequently, through the use of the band 3 having the aforedescribed construction, the instrument main body 2 can be brought into intimate contact with the surface of the body (the wrist) on the horizontal and with proper pressure, and highly reliable pulse data with minimal noise can be obtained.

The biological information measurement device 1 according to the present embodiment described above has the following effects.

The first band member 4 and the second band member 5 are provided with expanding sections 43, 53 having pliability, and the expanding sections 43, 53 have the above-described first slits 435, 535 and pair of second slits 436, 536. Because of these slits, in the expanding sections 43, 53, planar twisting such that the gap in directions A1 and A2 of one of the second slits 436, 536 becomes wider than the gap of the other second slit 436, 536 is permitted; and rotation about a center axis in directions A1 and A2 is permitted as well. Because of this, incline (twisting) of the instrument main body 2 and the band 3 can be absorbed; and because the instrument main body 2 can follow the contours of the wrist on which it is worn, the instrument main body 2 can be brought into intimate contact against the body.

The first slits 435, 535 and pair of second slits 436, 536 also permit stretching of the expanding sections 43, 53 along directions A1 and A2. Because of this, when the first band member 4 and the second band member 5 are linked via the linking member 6, the stretched expanding sections 43, 53 attempt to return, whereby retightening of the band 3 can be carried out. Consequently, the instrument main body 2 can be brought into more intimate contact against the body.

Further, the sliding member 62 slides along direction A1 relative to the fixed member 61 which is fixed to the first band member 4, and the coil springs 65 urge the sliding member 62 in the opposite direction from direction A1. Because of this, sliding member 62 which has slid in direction A1 during linking of the band members 4, 5 by the linking member 6 attempts to return under the urging force of the coil springs 65, and therefore retightening of the band 3 together with the expanding sections 43, 53 can be carried out in a manner dependent on pressure of the instrument main body 2 against the body. Consequently, the instrument main body 2 can be pressed against the body at proper pressure, and the tightening force of the band 3 can be adjusted to and maintained at proper magnitude.

Also, relatively long coil springs are employed as the coil springs 65, and the spring multiplier is low as compared with ordinary rubbers. Because of this, the spring multiplier can be set with relative freedom, and proper tightening force that imposes no undue burden on the body can be retained for extended periods.

Further, the design of the linking member 6 is comparable to that of the buckle of an ordinary wristwatch. Because of this, the contraction function provided by the linking member 6 can be exhibited even if modifications are made to the material and construction of the band which is attached to the linking member 6.

Also, the expanding sections 43, 53 for absorbing incline of the instrument main body 2 are formed at symmetrical positions to either side of the instrument main body 2, and where the band 3 is worn on the wrist, the linking member 6 which expands along direction A1 will be positioned to the opposite side from the instrument main body 2 with respect to the wrist. Because of this, the band members 4, 5 can exert uniform tensile force on the instrument main body 2 contacting the body in a region where expansion is relatively difficult. Consequently, the instrument main body 2 can be brought into stable intimate contact on the horizontal against the wrist.

Further, by furnishing the linking member 6 in addition to the expanding sections 43, 53, the area for retightening by the band 3 can be dispersed. Consequently, the urethane material is not readily subjected to stress, and the durability of the band 3 made of the urethane material or the like can be improved.

The expanding section 43 has the first connecting section 431, the second connecting section 432, and the U-shaped sections 433, 434, and by combination of these in the above-described manner, the first slits 435 having the pair of slits 4351 lying along direction B and the slit 4352 lying along direction A1, and the pair of second slits 436 communicating with the outside of the expanding section 43 along direction B can be reliably formed in the expanding section 43. The expanding section 53, which has a comparable configuration, has a comparable effect.

The fixed member 61 is furnished with the indicator section 6135 in which are made two points P1, P2 depicting a proper range of sliding of the sliding member 62. Because of this, by verifying that the end section at the first band member 4 side of the sliding member 62 is positioned between the points P1 and P2 using the amount of slide of the sliding member 62 as a guide, it can be verified whether proper tensile force is being exerted on the band 3. Consequently, because it can be verified that the instrument main body 2 is being worn at the proper pressure against the body, adverse effects on the body due to excessive tightening or impaired tightening functionality of the band 23 can be prevented.

Sliding of the sliding member 62 in direction A1 is guided through a combination of the protruding sections 6123, 6133 formed on the fixed member 61 and the pair of recessed sections 629 formed in the sliding member 62, and therefore the sliding member 62 can be made to slide in a stable manner. Also, because of this, twisting and travel of the sliding member 62 along direction B can be restricted. Consequently, even in a case where the linking member 6 is formed of synthetic resin with relatively low strength, the strength of the linking member 6 can be increased, and therefore the linking member 6 can be lighter and manufactured cheaper.

The excess portion of the second band member 5 with the projecting rod 63 inserted through a hole 511 is uplifted in a direction away from the first band member 4 by the uplifting sections 627. Because of this, contact between the fixed member 61, the first band member 4, and the second band member 5 can be prevented, and therefore sliding resistance of the sliding member 62 mating with the second band member via the projecting rod 63 can be reduced. Consequently, sliding of the sliding member 62 can be carried out in a reliable manner.

The pipe 72 is rotatably furnished to the restraining section 712 of the band guide 7. Because of this, in a case where the second band member 5 is inserted into the opening 711 and the sliding member 62 slides, frictional resistance between the edges of the opening 711 and the second band member 5 can be lower. Consequently, sliding resistance of the sliding member 62 can be even lower, and sliding of the sliding member 62 can be carried out in a more reliable manner.

The second attachment section 442 of greater thickness than the band main body 41 is formed in the first band member 4, and holes 4421 for insertion of the distal ends of the curving sections 713 are formed on side faces of the second attachment section 442 that do not contact the body. Because of this, direct contact of the band guard 7 with the body can be prevented. Consequently, application of unwanted pressure to the body can be prevented.

Modifications of the Embodiment

The invention is not limited to the above-described embodiment, and various modifications and improvements are included within the invention such that the advantages of the invention are still attainable.

In the aforedescribed embodiment, a projecting rod 63 that inserts into holes 511 in the second band member 5 was employed as the linking section, but the invention is not limited thereto. Specifically, other configurations are acceptable, provided that the configuration is one that is linkable with the second band member. For example, a configuration for clasping the second band member to link with the second band member is acceptable.

In the aforedescribed embodiment, points P1, P2 which depict the proper sliding range of the sliding member 62 are made in the indicator section 6135, but the invention is not limited thereto. Specifically, a configuration in which graduations are made in the indicator section is also acceptable.

In the aforedescribed embodiment, the configuration was one in which the fixed member 61 has protruding sections 6123, 6133, and the sliding member 62 has recessed sections 629, but the invention is not limited thereto, and instead the fixed member 61 may have recessed sections while the sliding member 62 has protruding sections. Also, the number and positions of the protruding sections and recessed sections may be established appropriately. Further, these protruding sections and recessed sections may be omitted entirely.

In the aforedescribed embodiment, the band guide 7 was attached to holes 4421 formed in side faces of the second attachment section 442, but the invention is not limited thereto. For example, the band guide may be furnished slidably along the first band member 4, like the moveable loop of a watchband. Further, the band guide 7 may be fixed to the first band member 4 on the body-facing face thereof.

In the configuration in the aforedescribed embodiment, a pair of coil springs 65 are furnished as urging members, but the invention is not limited thereto. Specifically, a single coil spring, or three or more, may be provided instead. Further, the urging member is not limited to a compression spring, and provided that the member can exert urging force, a tensile spring is also acceptable, as are springs of other types, and elastic components such as rubber.

In the configuration in the aforedescribed embodiment, the band 3 was employed for a biological information measurement device 1, but the invention is not limited thereto, and the invention may be employed in a band for wristwatches or the like. The wear position of the instrument main body 2 is not limited to the wrist, and may be a predetermined position of the body such as the ankle.

What is claimed is:

1. A band for attaching an instrument main body of an electronic instrument to a human body, the band comprising:
   a first band member and a second band member respectively attached to the instrument main body; and
   a linking member provided to the first band member at an end opposite from the instrument main body, the linking member adapted for linking together the first band member and the second band member;
   each of the first band member and the second band member including an expanding section that expands along a band extension direction coincident with the direction of extension thereof from the instrument main body,
   the expanding section being formed of material having pliability, the expanding section having
    first slits having a pair of slits lying along the width direction of the band member and a slit lying along the band extension direction and connecting the pair of slits, and
    a pair of second slits formed in locations sandwiched between the pair of slits and lying along the width direction of the band member to communicate with the outside of the expanding section,
the linking member having
    a fixed member fixed to the first band member,
    a sliding member slidably furnished relative to the fixed member along the band extension direction of the first band member, the sliding member having a pair of side portions each of which extends along the band extension direction, and
    an urging member disposed between the fixed member and the sliding member, the urging member adapted for urging the sliding member in the opposite direction from the band extension direction of the first band member, the urging member having a pair of urging portions each of which extends along the band extension direction,
the side portions of the sliding member including groove sections that accommodate the urging portions of the urging member therein, respectively
the sliding member having a linking section for linking with the second band member.

2. The band according to claim 1, wherein
the expanding section has
    a first connecting section positioned to the instrument main body side,
    a second connecting section positioned to the opposite side from the instrument main body side, and
    a first U-shaped section and a second U-shaped section respectively connected by the first connecting section and the second connecting section;
each of the first connecting section and the second connecting section has
    a basal section lying along the width direction of the band member having the expanding section, and
    a pair of extending sections extending along the band extension direction of the band member from either end of the basal section;
the first U-shaped section and the second U-shaped section are disposed across a predetermined gap such that bottom sections of the respective U shapes are in mutual opposition;
of the respective pairs of extending sections of the first connecting section and the second connecting section, the extending sections situated towards one end in the width direction of the band member connect respectively to a distal end of the U shape in the U-shaped section that, of the first U-shaped section and the second U-shaped section, is the section situated towards the one end, while the extending sections situated towards another end connect respectively to a distal end of the U shape in the U-shaped section that, of the first U-shaped section and the second U-shaped section, is the section situated towards the another end;
the first slits are formed between the first connecting section and the second connecting section, and between the first U-shaped section and the second U-shaped section; and
the second slits are formed between the distal ends of the first U-shaped section and between the distal ends of the second U-shaped section.

3. The band according to claim 1, wherein
the fixed member has an indicator section for indicating the amount by which the sliding member slides.

4. The band according to claim 1, wherein
either the fixed member or the sliding member has a protruding section formed along the sliding direction of sliding member, while the other has a recessed section that mates with the protruding section.

5. The band according to claim 4, wherein
the protruding section is configured to guide the recessed section along the band extension direction such that the sliding member slidably moves relative to the fixed member along the band extension direction.

6. The band according to claim 4, wherein
the protruding section protrudes from one of the fixed member and the sliding member in a perpendicular direction perpendicular to the band extension direction and the width direction.

7. The band according to claim 1, wherein the linking section is a projecting rod for passing through a hole formed in the second band member; and
    the sliding member is provided with uplifting sections positioned towards the first band member side relative to the projecting rod, the uplifting sections adapted for uplifting the second band member having the projecting rod passed through the hole.

8. The band according to claim 1, wherein the first band member is provided with a band guide for disposing, along the first band member, the end section of the second band member in the band extension direction of the second band member;
    the band guide is provided with
        a main section attached to the first band member, and
        a pipe rotatably furnished to the main section;
    the main section has
        a restraining section lying along the width direction of the first band member, and
        curving sections that respectively curve in the same direction from either end of the restraining section;
    with the band guide attached to the first band member, an opening section through which the second band member is inserted is formed by the first band member and the main section; and
    the pipe is rotatably furnished to the restraining section, such that an axis of rotation of the pipe lies along the width direction of the first band member.

9. The band according to claim 8, wherein
the first band member has a thick section; and
holes into which the distal ends of the curving sections are inserted are formed on side faces lying along the band extension direction of the first band member in the thick section and orthogonal to the width direction of the first band member.

10. An electronic instrument comprising:
an instrument main body for contacting a human body and measuring biological information; and
the band according to claim 1, attached to the instrument main body.

11. The band according to claim 1, wherein
the linking member has a buckle structure that is formed of the fixed member and the sliding member.

12. The band according to claim 1, wherein
the side portions partially define an opening for allowing the second band member to pass through herein.

* * * * *